(12) United States Patent
DeBolt

(10) Patent No.: US 6,306,102 B1
(45) Date of Patent: Oct. 23, 2001

(54) REFLEX TIMING DEVICE

(76) Inventor: Donald Lloyd DeBolt, 865 E. 5550 South, Ogden, UT (US) 84405

( * ) Notice: Subject to any disclaimer, the term of this patent is extended or adjusted under 35 U.S.C. 154(b) by 0 days.

(21) Appl. No.: 09/405,975

(22) Filed: Sep. 27, 1999

Related U.S. Application Data

(60) Provisional application No. 60/102,004, filed on Sep. 28, 1998.

(51) Int. Cl.$^7$ ........................................................ A61B 5/00
(52) U.S. Cl. ............................................................. 600/558
(58) Field of Search ................................... 600/558, 587, 600/595

(56) References Cited

U.S. PATENT DOCUMENTS

| | | | |
|---|---|---|---|
| 3,563,230 | * | 2/1971 | Gibbs .................................... 600/558 |
| 4,058,113 | * | 11/1977 | Fields .................................... 600/558 |
| 4,169,592 | * | 10/1979 | Hall ....................................... 600/558 |

FOREIGN PATENT DOCUMENTS

| | | | |
|---|---|---|---|
| 1165136 | * | 9/1969 | (GB) . |
| 93/16637 | * | 9/1993 | (WO) . |

* cited by examiner

Primary Examiner—Max Hindenburg
(74) Attorney, Agent, or Firm—Thompson E. Fehr

(57) ABSTRACT

A reflex timing device having a first switch. Engagement of the first switch causes a microcontroller to activate a second visual indicator at a random time. The micorcontroller measures the time between activation of the second visual indicator and engagement of a second switch. This measured time is compared by the microcontroller with a required benchmark reflex time, which may optionally be selected from several benchmark reflex times. A signal indicating success is provided if a subject being tested does not disengage said first switch until said second visual indicator has been activated and if the subject also engages said second switch within the required benchmark reflex time. Optionally, a signal indicated failure may be provided if these conditions have not been met.

28 Claims, 2 Drawing Sheets

REFLEX TIMING DEVICE

CROSS-REFERENCE TO RELATED APPLICATION

This is a continuation of a copending U.S. provisional application serial no. 60/102,004, filed on Sep. 28, 1998.

BACKGROUND OF THE INVENTION

1. Field of the Invention

This invention relates to a device and method for determining the time which it takes for a test subject to recognize and react to a visual signal.

2. Description of the Related Art

The inventor has been unable to locate a similar device.

A number of patents determine the speed with which a signal travels along a nerve or through skin and then along a nerve. These include U.S. Pat. Nos. 4,064,870; 4,807,643; 5,215,100; 5,313,956; and 5,388,587.

U.S. Pat. No. 4,570,640 covers a device that stimulates the skin of a test subject and then monitors the output side of the subject's central nervous system in order to determine the level and depth of spinal and epidural nerve blocks affecting the sympathetic and motor nervous system.

U.S. Pat. No. 5,263,490 discloses and claims a device that applies an electrical stimulus to a person's ulnar nerve and then measures the relaxation rate of the abductor pollicis muscle by determining the force exerted by the patient's thumb.

U.S. Pat. No. 5,381,805 deals with a device that administers "cutaneous stimulation" to a patient.

And U.S. Pat. No. 5,551,446 applies a stimulus (only a physical force is disclosed, although it is stated—but not explained—that such stimulus could be noise, light, or electrical shock) to a patient and measures the beginning of the patient's physical response to such stimulus.

Only this latter patent is intended to measure a reflex; and it simply measures an automatic reaction to a stimulus, not a response by a subject that requires both perception of a stimulus and a consciously directed response to that stimulus.

SUMMARY OF THE INVENTION

The present Reflex Timing Device requires the test subject to hold a first switch in a closed position until provided with a visual stimulus at which time the subject is to release the first switch and engage a second switch.

The time at which the visual stimulus is provided is randomly generated within set limits. The time between provision of the visual stimulus and engagement of the second switch is measured. And such time is compared with a required benchmark that has been selected by the operator of the Reflex Timing Device prior to administering the test to the subject.

If the subject does not release the first switch until the visual stimulus has been provided and engages the second switch within the selected time, a visual indication of success will be provided; otherwise, there will be a visual indication of failure.

DESCRIPTION OF THE PREFERRED EMBODIMENT

Figure 1:
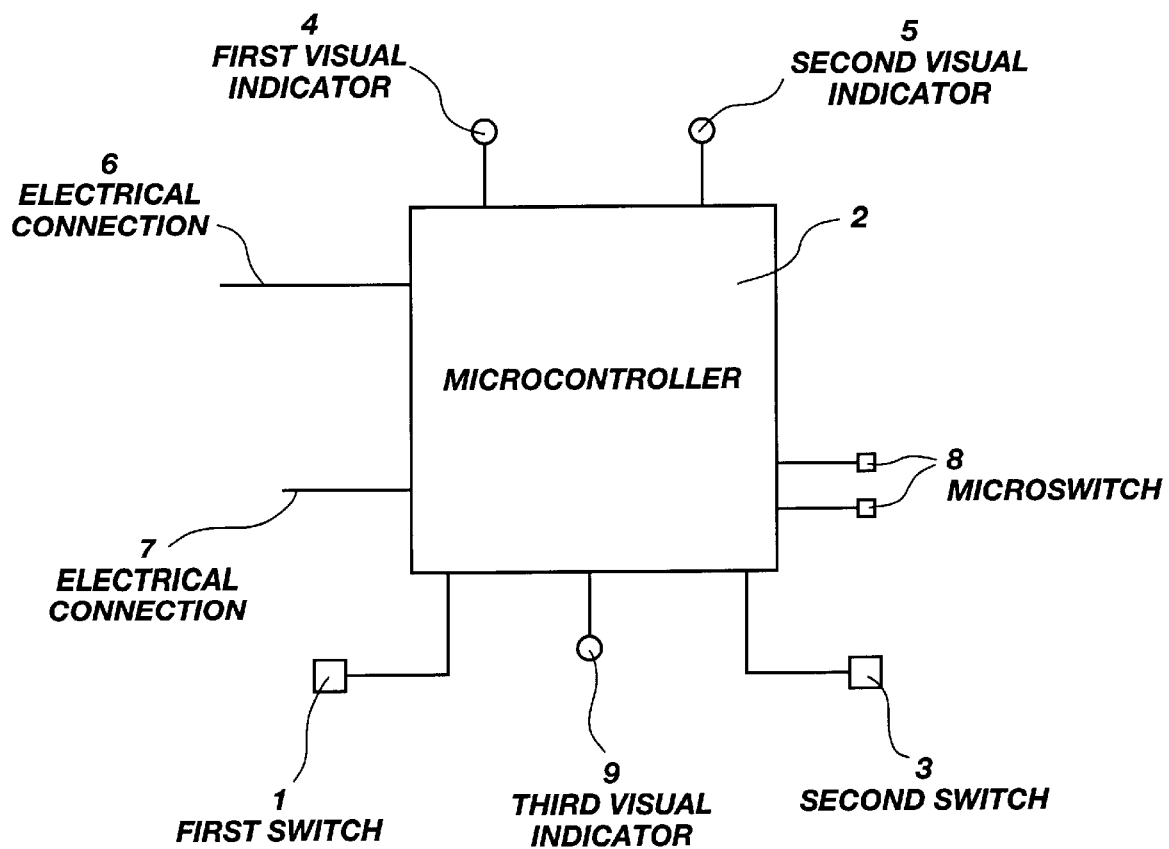
FIG. 1 is a block diagram of the Reflex Timing Device.

The Reflex Timing Device has a first switch 1, preferably a push-button switch, that is engaged only while being forcibly contacted—preferably, depressed. This first switch 1 is in electrical communication with a microcontroller 2, such as Microchip 8-pin microcontroller PIC12C509-04/P.

A second switch 3, preferably a push-button switch, is also in electrical communication with microcontroller 2.

Additionally in electrical communication with the microcontroller 2 are a first visual indicator 4, preferably a green light-emitting diode, and a second visual indicator 5, preferably a red light-emitting diode.

Upon power being furnished to the microcontroller 2, either from an electrical connection 6 to a standard wall receptacle or an electrical connection 7 to a battery, the Reflex Timing Device is ready to be used to test a subject.

The test subject is instructed to use only one hand, to engage (preferably, depressor the first switch 1 until the second visual indicator 5 is activated, then to disengage (preferably, cease depressing) the first switch 1, and subsequently to engage (preferably, press) the second switch 3. When the first switch 1 is engaged, a constant visual signal is displayed by the first visual indicator 4, i.e., preferably the green light-emitting diode is continuously illuminated.

The microcontroller 2 is programmed to generate an electrical signal that activates the second visual indicator 5 at a random time between a first period, preferably three seconds, and a longer second period, preferably ten seconds, after engagement of the first switch 1.

The microcontroller 2 is further programmed to measure the duration of time between activation of the second visual indicator 5 and engagement of the second switch 3. (The time that it takes a subject to recognize that the second visual indicator 5 has been activated is termed the "perception time," and the time required for the subject to disengage the first switch 1 and engage the second switch 3 is called the "reaction time." The combination of the perception time and the reaction time is denominated the "reflex time." It is the reflex time that is measured by the microcontroller 2.)

A required benchmark reflex time is programmed into the microcontroller 2. Preferably, the microcontroller 2 is programmed with multiple (preferably, three) benchmark reflex times. The operator of the Reflex Timing Device can utilize any device that is well known in the art to select the desired benchmark reflex time to be used; preferably, the operator appropriately positions one or more microswitches 8 (preferably, two) that are in electrical communication with the microcontroller 2; and preferably each microswitch 8 has two possible settings.

The microcontroller 2 is further programmed to compare the measured reflex time against the selected benchmark reflex time. And the microcontroller is additionally programmed so that if the subject does not disengage the first switch 1 until the second visual indicator 5 has been activated and if the subject also engages the second switch 3 within the selected benchmark reflex time, a signal indicating success will be produced, preferably a signal that will intermittently activate the first visual indicator 4 (preferably, cause the green light-emitting diode to flash). Otherwise, the program will cause the microcontroller to generate a signal indicating failure, preferably a signal that will intermittently activate the second visual indicator 5 (preferably, cause the red light-emitting diode to flash).

Finally, the microcontroller 2 is programmed so that simultaneous engagement of the first switch 1 and the second switch 3 will cause the microcontroller to deactivate the first visual indicator 4 as well as the second visual indicator 5 and to determine which benchmark reflex time has been selected to serve as the required benchmark reflex time so that the Reflex Timing Device is again ready to be used upon a test subject.

Preferably, a third visual indicator 9, preferably a yellow light-emitting diode will is located electrically so that it will be activated whenever electrical power is supplied to the Reflex Timing Device.

Figure 2:
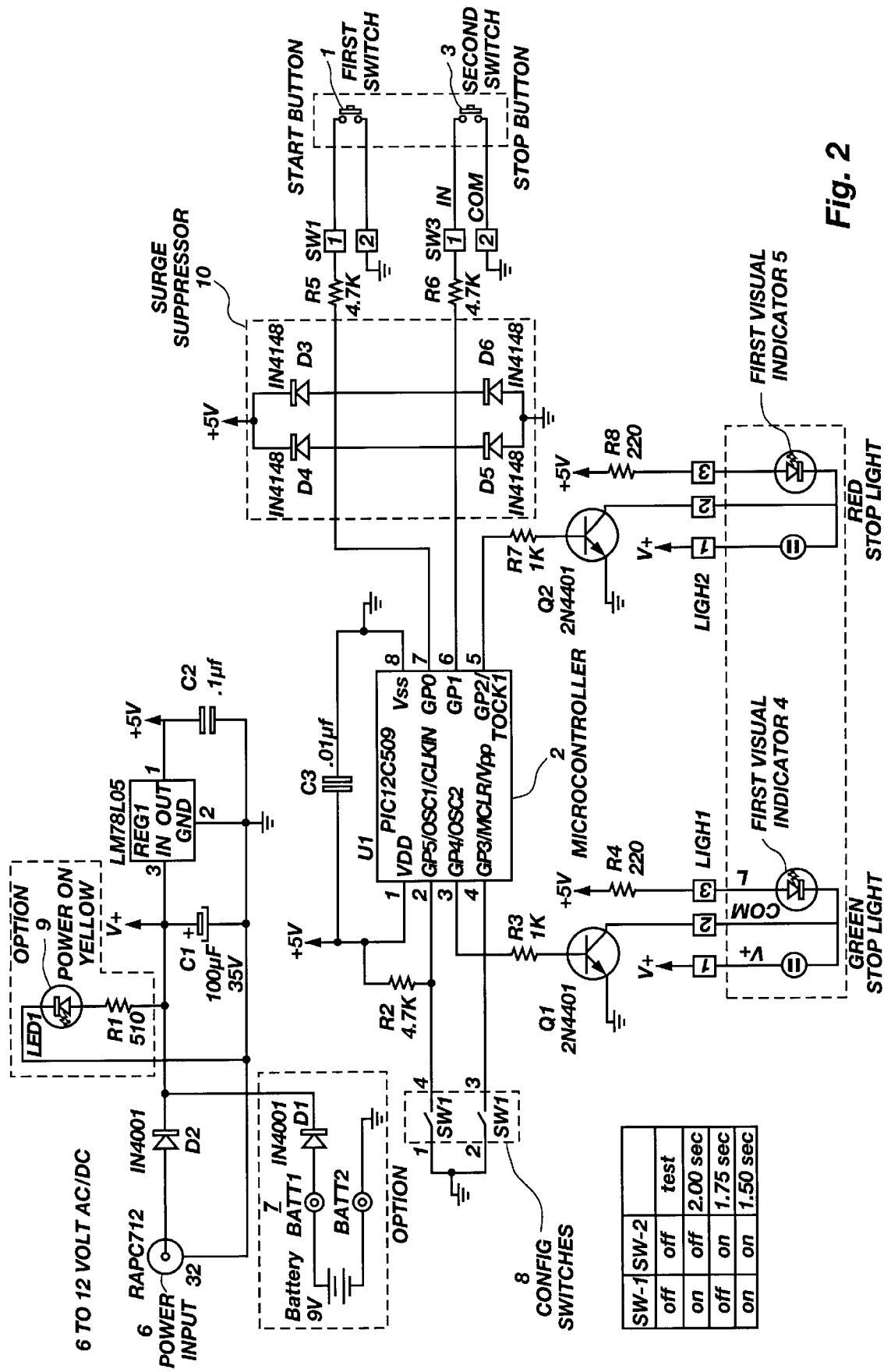
FIG. 2 gives the electrical schematic for the Reflex Timing Device upon which the principal functional components have been indicated.

And, as shown in FIG. 2, it is preferable to have a surge suppressor 10 between the microcontroller 2 and both the first switch 1 and the second switch 3.

I claim:

1. A reflex timing device, which comprises:
   first switch;
   a second switch;
   a first visual indicator;
   a second visual indicator; and
   a microcontroller in electrical communication with said first switch, with said second switch, with said first visual indicator, and with said second visual indicator, said microcontroller being programmed to generate an electrical signal that activates said second visual indicator at a random time between a first period and a longer second period after engagement of the first switch, to measure the reflex time by measuring the duration of time between activation of the second visual indicator and engagement of said second switch, to contain a required benchmark reflex time, to compare the measured reflex time against the required benchmark reflex time, and to produce a signal indicating success if a subject being tested does not disengage said first switch until said second visual indicator has been activated and if the subject also engages said second switch within the required benchmark reflex time.

2. The reflex timing device as recited in claim 1, wherein:
   said microcontroller is further programmed to produce a signal indicating failure if the test subject either disengages said first switch before said second visual indicator has been activated or does not engage said second switch within the required benchmark reflex time.

3. The reflex timing device as recited in claim 2, wherein:
   said microcontroller is programmed with additional benchmark reflex times; and
   said reflex timing device further comprises a means for selecting which of the benchmark reflex times will serve as the required benchmark reflex time.

4. The reflex timing device as recited in claim 3, wherein:
   said microcontroller is programmed with two additional benchmark reflex times; and
   said means for selecting which of the benchmark reflex times will serve as the required benchmark reflex time comprises two microswitches that are in electrical communication with said microcontroller, each of which microswitches has two possible settings.

5. The reflex timing device as recited in claim 3, wherein:
   said microcontroller is programmed so that simultaneous engagement of said first switch and said second switch will cause the microcontroller to deactivate said first visual indicator as well as said second visual indicator and to determine which benchmark reflex time has been selected to serve as the required benchmark reflex time so that said reflex timing device is again ready to be used upon a test subject.

6. The reflex timing device as recited in claim 5, wherein:
   said microcontroller is programmed with two additional benchmark reflex times; and
   said means for selecting which of the benchmark reflex times will serve as the required benchmark reflex time comprises two microswitches that are in electrical communication with said microcontroller, each of which microswitches has two possible settings.

7. The reflex timing device as recited in claim 5, wherein:
   said first switch is a push-button switch that is engaged only while being depressed; and
   said second switch is a push-button switch.

8. The reflex timing device as recited in claim 7, wherein:
   said microcontroller is programmed with two additional benchmark reflex times; and
   said means for selecting which of the benchmark reflex times will serve as the required benchmark reflex time comprises two microswitches that are in electrical communication with said microcontroller, each of which microswitches has two possible settings.

9. The reflex timing device as recited in claim 7, wherein:
   said first visual indicator is a green light-emitting diode;
   said second visual indicator is a red light-emitting diode;
   a signal indicating success generated by said microcontroller causes said first visual indicator to flash; and
   a signal indicating failure generated by said microcontroller causes said second visual indicator to flash.

10. The reflex timing device as recited in claim 9, wherein:
    said microcontroller is programmed with two additional benchmark reflex times; and
    said means for selecting which of the benchmark reflex times will serve as the required benchmark reflex time comprises two microswitches that are in electrical communication with said microcontroller, each of which microswitches has two possible settings.

11. The reflex timing device as recited in claim 5, wherein:
    said first visual indicator is a green light-emitting diode;
    said second visual indicator is a red light-emitting diode;
    a signal indicating success generated by said microcontroller causes said first visual indicator to flash; and
    a signal indicating failure generated by said microcontroller causes said second visual indicator to flash.

12. The reflex timing device as recited in claim 11, wherein:
    said microcontroller is programmed with two additional benchmark reflex times; and
    said means for selecting which of the benchmark reflex times will serve as the required benchmark reflex time comprises two microswitches that are in electrical communication with said microcontroller, each of which microswitches has two possible settings.

13. The reflex timing device as recited in claim 3, wherein:
    said first switch is a push-button switch that is engaged only while being depressed; and
    said second switch is a push-button switch.

14. The reflex timing device as recited in claim 13, wherein:
    said microcontroller is programmed with two additional benchmark reflex times; and
    said means for selecting which of the benchmark reflex times will serve as the required benchmark reflex time comprises two microswitches that are in electrical communication with said microcontroller, each of which microswitches has two possible settings.

15. The reflex timing device as recited in claim 13, wherein:

said first visual indicator is a green light-emitting diode;

said second visual indicator is a red light-emitting diode;

a signal indicating success generated by said microcontroller causes said first visual indicator to flash; and a signal indicating failure generated by said microcontroller causes said second visual indicator to flash.

16. The reflex timing device as recited in claim 15, wherein:

said microcontroller is programmed with two additional benchmark reflex times; and said means for selecting which of the benchmark reflex times will serve as the required benchmark reflex time comprises two microswitches that are in electrical communication with said microcontroller, each of which microswitches has two possible settings.

17. The reflex timing device as recited in claim 3, wherein:

said first visual indicator is a green light-emitting diode;

said second visual indicator is a red light-emitting diode;

a signal indicating success generated by said microcontroller causes said first visual indicator to flash; and a signal indicating failure generated by said microcontroller causes said second visual indicator to flash.

18. The reflex timing device as recited in claim 17, wherein:

said microcontroller is programmed with two additional benchmark reflex times; and said means for selecting which of the benchmark reflex times will serve as the required benchmark reflex time comprises two microswitches that are in electrical communication with said microcontroller, each of which microswitches has two possible settings.

19. The reflex timing device as recited in claim 2, wherein:

said microcontroller is programmed so that simultaneous engagement of said first switch and said second switch will cause the microcontroller to deactivate said first visual indicator as well as said second visual indicator and to determine which benchmark reflex time has been selected to serve as the required benchmark reflex time so that said reflex timing device is again ready to be used upon a test subject.

20. The reflex timing device as recited in claim 19, wherein:

said first switch is a push-button switch that is engaged only while being depressed; and said second switch is a push-button switch.

21. The reflex timing device as recited in claim 20, wherein:

said first visual indicator is a green light-emitting diode;

said second visual indicator is a red light-emitting diode;

a signal indicating success generated by said microcontroller causes said first visual indicator to flash; and a signal indicating failure generated by said microcontroller causes said second visual indicator to flash.

22. The reflex timing device as recited in claim 19, wherein:

said first visual indicator is a green light-emitting diode;

said second visual indicator is a red light-emitting diode;

a signal indicating success generated by said microcontroller causes said first visual indicator to flash; and a signal indicating failure generated by said microcontroller causes said second visual indicator to flash.

23. The reflex timing device as recited in claim 2, wherein:

said first switch is a push-button switch that is engaged only while being depressed; and said second switch is a push-button switch.

24. The reflex timing device as recited in claim 23, wherein:

said first visual indicator is a green light-emitting diode;

said second visual indicator is a red light-emitting diode;

a signal indicating success generated by said microcontroller causes said first visual indicator to flash; and a signal indicating failure generated by said microcontroller causes said second visual indicator to flash.

25. The reflex timing device as recited in claim 2, wherein:

said first visual indicator is a green light-emitting diode;

said second visual indicator is a red light-emitting diode;

a signal indicating success generated by said microcontroller causes said first visual indicator to flash; and a signal indicating failure generated by said microcontroller causes said second visual indicator to flash.

26. A reflex timing device, which comprises:

a first switch;

a second switch;

a second visual indicator; and a microcontroller in electrical communication with said first switch, with said second switch, and with said second visual indicator, said microcontroller being programmed to generate an electrical signal that activates said second visual indicator at a random time between a first period and a longer second period after engagement of said first switch, to measure the reflex time by measuring the duration of time between activation of the second visual indicator and engagement of the second switch, to contain a required benchmark reflex time, to compare the measured reflex time against the required benchmark reflex time, and to produce a signal indicating failure if the test subject either disengages said first switch before said second visual indicator has been activated or does not engage said second switch within the required benchmark reflex time.

27. A process for use by an operator for determining the adequacy of the reflex time of a test subject, which comprises:

having the test subject use only one hand to perform the process;

having the test subject engage a first switch;

then activating a second visual indicator at a random time between a first period and a longer second period;

having the test subject disengage the first switch and engage a second switch when the test subject perceives that the second visual indicator has been activated;

measuring the reflex time by measuring the duration of time between activation of the second visual indicator and engagement of the second switch;

comparing the measured reflex time against a required benchmark reflex time; and indicating failure if the test subject either disengages said first switch before said second visual indicator has been activated or does not engage said second switch within the required benchmark reflex time.

28. A process for use by an operator for determining the adequacy of the reflex time of a test subject, which comprises:

having the test subject use only one hand to perform the process;

having the test subject engage a first switch that is a push-button switch that is engaged only while being depressed;

then activating a red light-emitting diode at a random time between a first period and a longer second period;

having the test subject disengage the first push-button switch and engage a second push-button switch when the test subject perceives that the red light-emitting diode has been activated;

measuring the reflex time by measuring the duration of time between activation of the red light-emitting diode and engagement of the second push-button switch;

selecting a required benchmark reflex time;

comparing the measured reflex time against the required benchmark reflex time;

flashing a green light-emitting diode indicating success if a subject being tested does not disengage said first switch until said second visual indicator has been activated and if the subject also engages said second switch within the required benchmark reflex time; and flashing a red light-emitting diode indicating failure if the test subject either disengages said first switch before said second visual indicator has been activated or does not engage said second switch within the required benchmark reflex time.

\* \* \* \* \*